United States Patent
Keropian

(10) Patent No.: US 7,861,722 B2
(45) Date of Patent: Jan. 4, 2011

(54) SLEEP APPLIANCE

(76) Inventor: Bryan Keropian, 18663 Ventura Blvd., Suite 200, Tarzana, CA (US) 91356

( * ) Notice: Subject to any disclaimer, the term of this patent is extended or adjusted under 35 U.S.C. 154(b) by 296 days.

(21) Appl. No.: 12/102,239

(22) Filed: Apr. 14, 2008

(65) Prior Publication Data

US 2008/0210244 A1    Sep. 4, 2008

Related U.S. Application Data

(63) Continuation-in-part of application No. 11/165,641, filed on Jun. 23, 2005, now Pat. No. 7,451,767.

(60) Provisional application No. 60/923,989, filed on Apr. 17, 2007.

(51) Int. Cl.
*A61F 5/56* (2006.01)
*A61C 5/14* (2006.01)
*A61C 3/00* (2006.01)

(52) U.S. Cl. .................. 128/848; 128/859; 128/860; 128/861; 128/862; 433/6; 433/7; 433/8

(58) Field of Classification Search ........... 128/848, 128/859, 860, 861, 862; 602/902; 433/6, 433/7, 8
See application file for complete search history.

(56) References Cited

U.S. PATENT DOCUMENTS

| 3,871,370 | A | 3/1975 | McDonald |
| 4,669,459 | A | 6/1987 | Spiewak |
| 4,901,737 | A | 2/1990 | Toone |
| 5,915,385 | A | 6/1999 | Hakimi |
| 6,467,484 | B1 * | 10/2002 | De Voss ............... 128/848 |
| 6,766,802 | B1 | 7/2004 | Keropian |
| 2005/0166928 | A1 | 8/2005 | Jiang |

* cited by examiner

*Primary Examiner*—Patricia M Bianco
*Assistant Examiner*—Nihir Patel
(74) *Attorney, Agent, or Firm*—Sanford Astor; Lewis Brisbois Bisgaard & Smith LLP

(57) ABSTRACT

A dental oral appliance to reduce or eliminate snoring or obstructive sleep apnea and to open the airway for a sleeping patient. The appliance covers the inside (lingual) of the upper or lower teeth and has an open palate. Retention for the appliance is provided by an occlusal coverge of the upper or lower teeth. A raised incisor ramp that extends from the incisal tip of the incisors toward the lingual, or posterior ramps, separate the posterior teeth to open the airway. A transpalatal bar, which extends from the inside (lingual) of the right molars to the inside of the left molars, inhibits the upward and backward movement of the tongue. An anterior tongue restrainer which is attached to the transpalatal bar at one end and the front of the appliance at the other end, aids in inhibiting and restraining the upward and backward movement of the tongue.

30 Claims, 5 Drawing Sheets

SLEEP APPLIANCE

This application claims the benefit of U.S. Provisional Application Ser. No. 60/923,989, filed Apr. 17, 2007, which application is incorporated herein by reference in its entirety.

TECHNICAL FIELD

This invention relates to an intra-oral device for reducing or eliminating snoring and/or sleep apnea.

BACKGROUND ART

The invention described in this application is an improvement over the devices described in my U.S. Pat. No. 6,766,802, issued on Jul. 27, 2004, U.S. application Ser. No. 11/165,641, filed Jun. 23, 2005, now U.S. Pat. No. 7,451,767, issued Nov. 18, 2008, and my PCT Application Serial Number PCT/US2007/011183, filed May 9, 2007, all of which are incorporated herein by reference in their entirety.

As stated in my U.S. patent referenced above, it has been estimated that ninety million American adults and children snore and that three in every ten adults snores. Snoring can have serious medical consequences for some people. Snoring is the first indication of a potentially life-threatening sleep disorder called Obstructive Sleep Apnea. If not diagnosed or if left untreated, Obstructive Sleep Apnea could result in severe medical consequences such as systemic high blood pressure, cardiovascular disease and even sudden death.

Obstructive sleep apnea occurs during sleep when the tongue falls and rolls upward and backward blocking the airway for 10-90 seconds. These events are measured by spending the night sleeping in a center which measures the number of air blockage events per hour. Less than 5 events per hour is normal. 5-19 events per hour is mild sleep apnea. 20-39 events per hour is moderate sleep apnea. Over 40 events per hour is severe sleep apnea. For sleep apnea there are three main treatments of choice: the CPAP machine, surgery and oral sleep appliances. They are all designed to open the airway during sleep so that there is minimal or no air blockage.

Snoring is caused by vibration of the tissues due to air turbulence as the airway narrows and may be a sign that a patient is suffering from apnea. But not all snorers suffer from apnea. Snoring can be categorized by its severity. There is the snorer who snores but experiences no physical problems. Then, there is the snorer who suffers from apnea, or the snorer who suffers from upper airway resistance. In some of these people, though they may not actually experience apneic episodes, their snoring is so loud and their breathing so labored, that it still wakes them, and their partners, numerous times throughout the night.

Many spouses, partners and/or children suffer through the night from the annoying noise of the snorer. Snoring not only disturbs the sleeping pattern of the snorer himself, it is also disruptive to the family life by causing lack of sleep to all involved. This leaves all involved unrefreshed, tired and sleepy throughout the day. It can cause sleepiness while driving, reading, working or doing other tasks.

A broad variety of intra-oral and dental appliances and devices are now available to treat a patient for snoring. Some known oral devices for treating snoring and obstructive sleep apnea are worn inside of the mouth and work by repositioning of the jaw, moving the mandible, lifting the soft palate or moving the tongue forward. The various classes of treatment devices that now exist include mandibular advancers and tongue advancers. These appliances work by pushing (advancing) the tongue and lifting the soft palate away from the back wall of the throat. Other methods used to treat snoring include controlled positive air-flow pressure systems, also known as CPAP, which require a nose mask and which are quite uncomfortable.

Other treatments for snoring include various surgeries, which are drastic steps to take to attempt to cure the problem, however snoring can be so disruptive to a person's life and relationships, that some sufferers resort to surgery.

BRIEF DESCRIPTION OF THE INVENTION

The sleep appliance of this invention is a dental oral appliance for use with patients who suffer with sleep disorders. Primarily it is designed to reduce or eliminate snoring and to open the airway for a sleeping individual who suffers with obstructive sleep apnea. One embodiment of the appliance is physically designed similar to an upper (maxillary) orthodontic retainer, commonly called a Hawley retainer. It covers the inside (lingual) of the upper teeth and has an open palate (nothing covering the middle area of the palate). The body of the appliance has a series of recesses to fit against the lingual side of the teeth.

Retention (holding ability) for the appliance is provided by acrylic fittings which hold the appliance in place in the same manner as an occlusal night guard.

In one embodiment, in the anterior area there is a raised strip or ramp that extends from the incisal tip (biting edge) of two or more of the incisors toward the lingual. It extends back a short distance from the incisors (where they meet or touch each other). This raised anterior strip acts as a bite discluder, to disclude or separate the posterior teeth.

In an additional embodiment there is no anterior ramp. The upper and lower teeth are separated by raised posterior ramps. This embodiment allows more room for the tongue to come forward, if desired.

There is a transverse strip, a transpalatal bar, that extends from the inside (lingual) of the upper or lower right molars to the inside of the upper or lower left molars. This transverse strip extends from the right to the left and covers the tongue. It does not touch the tongue unless the tongue attempts to move upward or backward, as often happens during sleep and causes snoring or sleep apnea. The transpalatal bar inhibits and restrains the upward and backward movement of the tongue, keeping the airway open during sleep.

Optionally, the transpalatal bar is slightly curved upward at its center, or it can be straight across, so that it does not touch the tongue but passes just over the tongue when the tongue is in its normal position. Also, the transpalatal bar does not touch the palate. By not touching either the tongue or the palate, the device of this invention is comfortable to wear and easily tolerated by patient users. Prior art devices, which have either pushed the tongue down or pressed the palate up, were found to be unusable, as they often either created a gag reflex by the user or were so uncomfortable that they were unable to be tolerated by the user. The exact radius of the curvature of the transpalatal bar is determined by the physical dimensions and structure of each individual patient's anatomy. Some patients may need little or no curvature to achieve optimum results and other patients may need more curvature. The object is to have the transpalatal bar not touch the tongue or the palate, so that it will be tolerated, but inhibit and restrain any upward or backward movement of the tongue during sleep.

In addition, in the devices of this invention, there is optionally a posterior tongue restrainer (a tail) that extends backward from the center of the transpalatal bar. This posterior tongue restrainer provides a further barrier to the tongue's superior and posterior movement that blocks the airway to the posterior portion of the mouth. The posterior tongue restrainer, like the transpalatal bar, does not touch the tongue in its normal position but does restrain and inhibit the upward and backward movement of the tongue during sleep. Also, the posterior tongue restrainer, like the transpalatal bar, does not touch the palate. This posterior tongue restrainer may be added to all of the appliances that are described in my issued patent, in my co-pending application and pending PCT patent application, set forth above. The need for a posterior tongue restrainer depends on the needs of the patient. There may be one posterior tongue restrainer or a plurality of posterior tongue restrainers extending back from the transpalatal bar.

There is an additional embodiment, which is an appliance that covers the lower teeth, as opposed to the upper teeth, and has a transpalatal canopy bar that arcs over the tongue from right to left. The transpalatal canopy bar arches upward toward the palate and provides a cover (restrainer) over the tongue, but it does not touch the palate. A posterior tongue restrainer may be added to this arched transpalatal bar. This arched transpalatal canopy bar does not touch the tongue or the palate but inhibits and restrains the upward and backward movement of the tongue during sleep.

In addition, the transpalatal bar, with or without the posterior tongue restrainer, in all versions of the appliance, may be made adjustable, anterior to posterior, by providing a slidable fit of the transpalatal bar, forward and backward. With this adjustment, the appliance can be customized to each patient, to provide the proper fit for inhibiting movement of the tongue of each patient at its maximum effectiveness.

The transpalatal bar may fit into slots or grooves on either side of the lingual (palate side) of the appliance and can slide forward and backward. Alternatively, the best location of the transpalatal bar can be determined by the doctor and then the bar can be cemented in place with acrylic. The position of the transpalatal bar is determined by the patient's comfort. If it bothers the patient and causes gagging, then it is slid forward. If there is no problem with comfort, it is moved all the way back. If it requires being slid forward, it is worn for a month or so in this position, then slid all the way back. In almost all cases, the patient can then tolerate the bar all the way back. When the optimum location of the bar is determined, it is then cemented into place with acrylic.

The improvement to my prior described sleep appliances comprises an anterior tongue restrainer. This restrainer is connected to the transpalatal bar at the rear of the appliance, preferably the middle of the transpalatal bar, and to either the incisor raised strip or ramp discussed above or to the anterior portion of the appliance, generally lingual of teeth 8 and 9. The anterior tongue restrainer may be straight or curved slightly downward. It does not touch the tongue in its normal position nor does it touch the palate but it does inhibit and restrain the upward and backward movement of the tongue.

To understand the effectiveness of the appliance, the mechanism of snoring and obstructive sleep apnea must be understood. While we sleep, the tongue falls back and up towards the palate and it partially or completely obstructs or closes the airway path. This results in snoring, obstructive sleep apnea, or Upper Airway Resistance Syndrome. The medical treatment for these maladies range from medication to a CPAP (Continuous Positive Airway Pressure) machine. The CPAP is nearly 100% successful when utilized. Unfortunately, the non-compliance for CPAP use ranges from 50% to 80% depending where one searches in the literature. The American Association of Sleep Medicine designated dental sleep appliances as the number one alternative to CPAP for mild and moderate sleep apnea.

The sleep appliance of this invention is designed to treat the problem of tongue blockage when sleeping. It works by utilizing several factors. First, it changes the vertical dimension (height of the opening or separation of the teeth). This results in an increased opening of the airway. Second, the transpalatal bar, the posterior tongue restrainer and the anterior tongue restrainer all act to effectively inhibit and restrain the upward and backward movement of the tongue, which would block the airway opening during sleep. Optionally, if needed, the sleep appliance can also include mandibular advancement to increase the opening, thus increasing the airway.

OBJECTS OF THE INVENTION

Accordingly, several objects and advantages of the invention are as follows:

It is an object of this invention to provide a simple device to prevent or reduce snoring as well as Obstructive Sleep Apnea.

It is another object of this invention to provide a device, easily applied and easily tolerated, which will substantially prevent snoring.

Further objects and advantages will become apparent from a consideration of the following description and drawings.

BEST MODE FOR CARRYING OUT THE INVENTION

Figure 1:
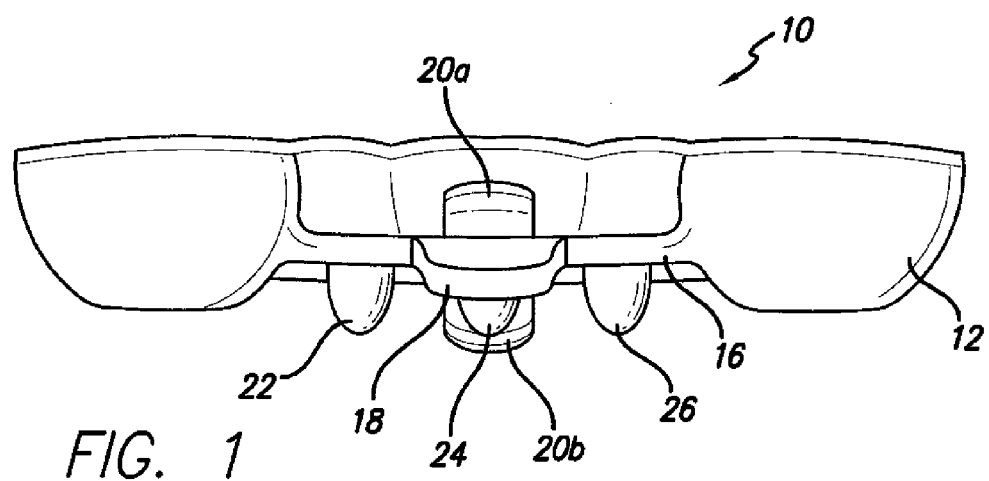
FIG. 1 is a rear elevation view of an embodiment of the improved sleep appliance of this invention.
Figure 2:
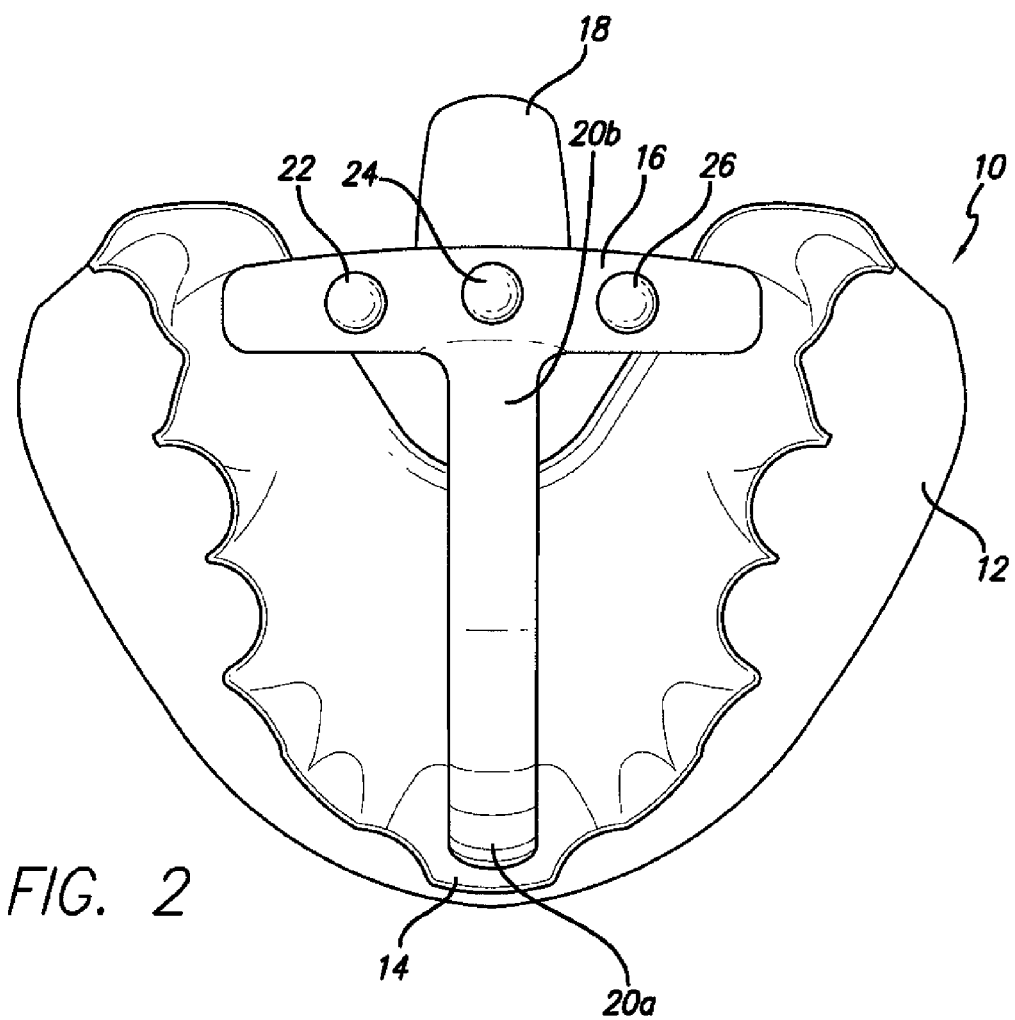
FIG. 2 is a bottom view of the embodiment of FIG. 1.
Figure 3:
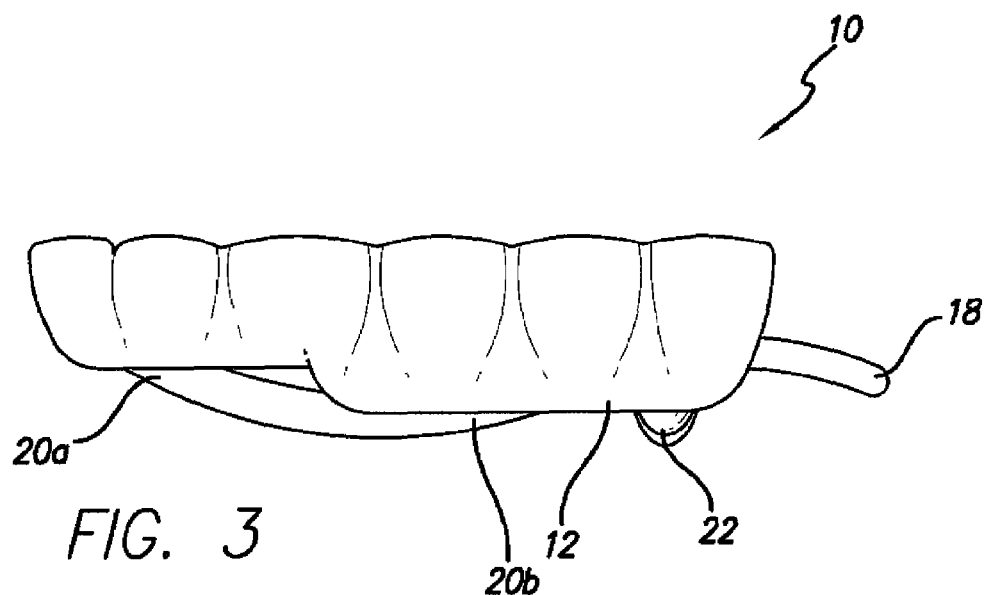
FIG. 3 is a side elevation view of the embodiment of FIG. 1.
Figure 4:
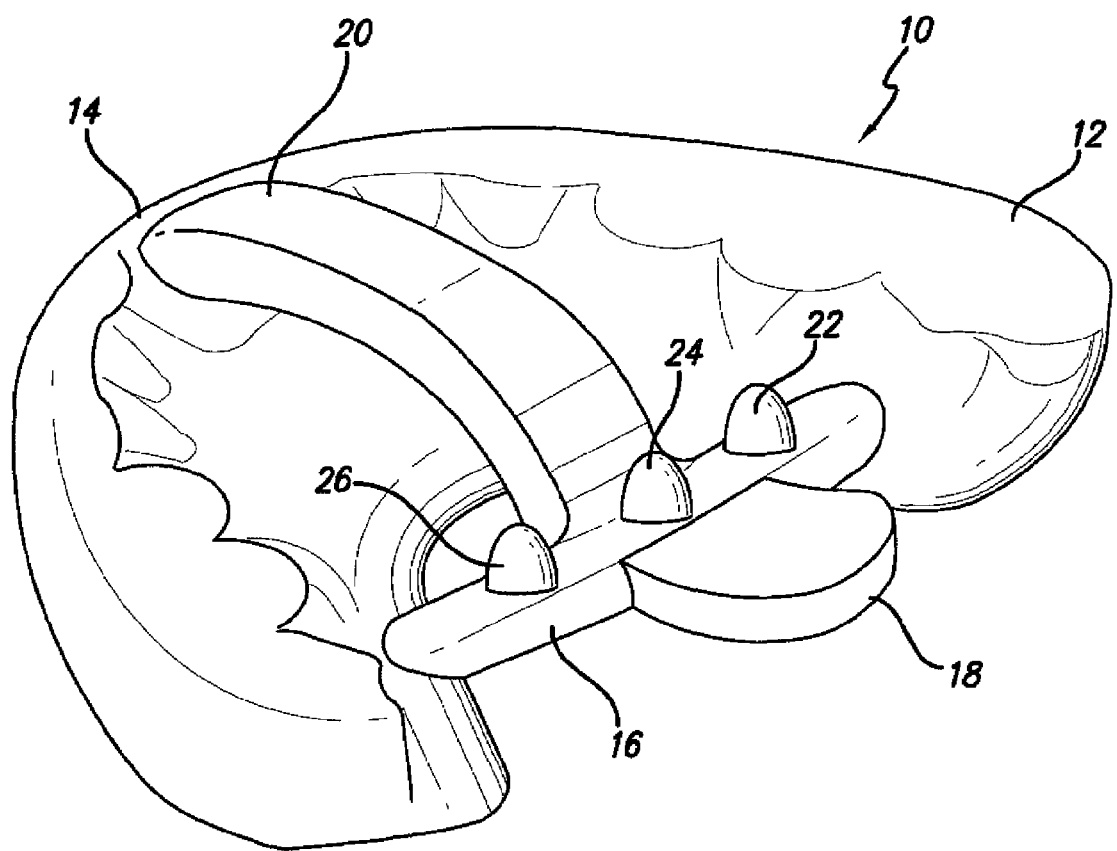
FIG. 4 is a perspective view of the embodiment of FIG. 1.

Referring now to FIGS. 1 through 4, there is shown a first embodiment 10 of the sleep appliance of this invention comprising a body 12. Body 12 is made entirely of an acrylic plastic, commonly used for dental devices, and is custom fitted to fit over the wearer's posterior teeth in the same manner as an occlusal night guard, which uses an occlusal coverage. The occlusal coverage holds appliance 10 firmly onto the posterior teeth.

There is a raised anterior strip 14 that extends from the incisal tip (biting edge) of two or more of the incisors toward the lingual. Strip 14 extends back a short distance from the middle of the central incisors. Strip 14 acts as a bite discluder, separating the posterior teeth. Strip 14 is preferably from about 3 mm to about 5 mm thick in order to separate the posterior teeth.

Transverse transpalatal bar 16 extends from the inside of the right upper molars to the inside of the left upper molars and inhibits the upward and backward movement of the tongue, to keep the airway open during sleep. Transpalatal bar 16 may be straight or curved slightly upwards over the tongue, depending upon the needs of the patient. Transpalatal bar 16 does not touch the tongue in its normal state and does not touch the palate, so that there is a gap between the transpalatal bar and the tongue and a gap between the transpalatal bar and the palate. Transpalatal bar 16 does inhibit and restrain the upward and backward movement of the tongue.

Posterior tongue restrainer 18 is attached to the center rear portion of transpalatal bar 16 and extends rearward, and may be straight or curved downward towards the tongue, depending upon the needs of the patient, to further inhibit the upward and backward movement of the tongue. Posterior tongue restrainer 18 also does not touch the tongue in its normal state and does not touch the palate.

Anterior tongue restrainer 20 extends from raised anterior strip 14 to transpalatal bar 16, to further inhibit and restrain the upward and backward movement of the tongue. Section 20(*a*) of anterior tongue restrainer 20 is the section that attaches to raised anterior strip 14. Section 20(*b*) of anterior tongue restrainer 20 is the section that curves downward, when desired for a particular patient. Anterior tongue restrainer 20 can either be straight or curved downward towards the tongue, depending upon the needs of the patient, however anterior tongue restrainer 20, (even if curved) does not touch the tongue in its normal state. It also does not touch the palate. It does help to inhibit and restrain the upward and backward movement of the tongue during sleep.

Anterior tongue restrainer 20 is attached to raised anterior strip 14 by the use of an acrylic. Anterior tongue restrainer 20 can be attached to transpalatal bar 16 by the use of an acrylic or it can be manufactured as a part of transpalatal bar 16, as a unit.

Posterior projections 22, 24 and 26 are optionally added to the bottom of transpalatal bar 16, to further inhibit the upward and backward movement of the tongue. Posterior projections 22, 24 and 26 are from about 1 mm to about 6 mm long depending upon the needs of the patient. While three projections are shown and are generally cylindrical in shape, any number, from about 2 to about 12 projections may be used and they may be any shape, such as rectangular, conical, oval, or any other shape. Posterior projections 22, 24 and 26 do not touch the tongue in its normal state, but further inhibit the upward and backward movement of the tongue during sleep.

Figure 5:
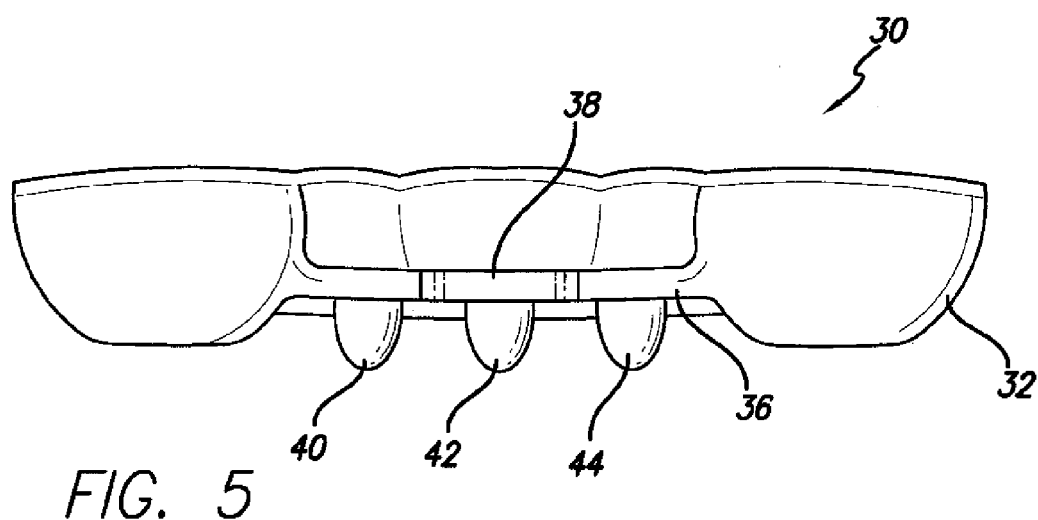
FIG. 5 is a rear elevation view of another embodiment of the invention.
Figure 6:
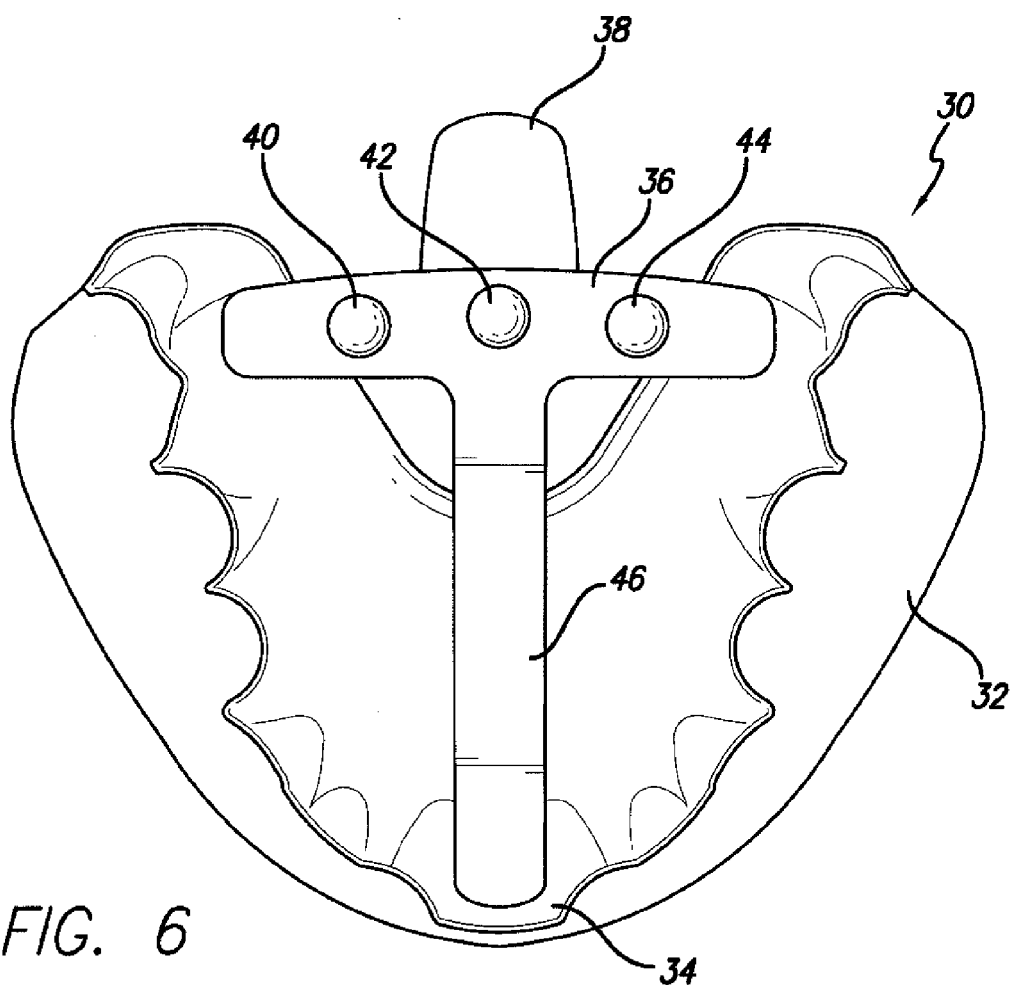
FIG. 6 is a bottom view of the embodiment of FIG. 5.

Referring to FIGS. 5 and 6 there is shown another embodiment of an appliance 30 with a body 32 and an anterior strip or ramp 34. This appliance is adapted to fit over the upper teeth, similar to the first embodiment described above. Body 32 is made entirely of an acrylic plastic, commonly used for dental devices, and is custom fitted to fit over the upper posterior teeth in the same manner as an occlusal night guard, which uses an occlusal coverage. The occlusal coverage holds appliance 30 firmly onto the upper posterior teeth.

Transpalatal bar 36 inhibits the upward and backward movement of the tongue as described for the first embodiment. Posterior tongue restrainer 38, is attached to the center rear portion of transpalatal bar 36 and extends rearward to further inhibit the upward and backward movement of the tongue. In this embodiment, transpalatal bar 36 and posterior tongue restrainer 38 are both straight, without any curve.

Posterior projections, 42, 44 and 46 may optionally also be present, if needed for the patient's benefit, to further inhibit and restrain the upward and backward movement of the tongue.

Figure 7:
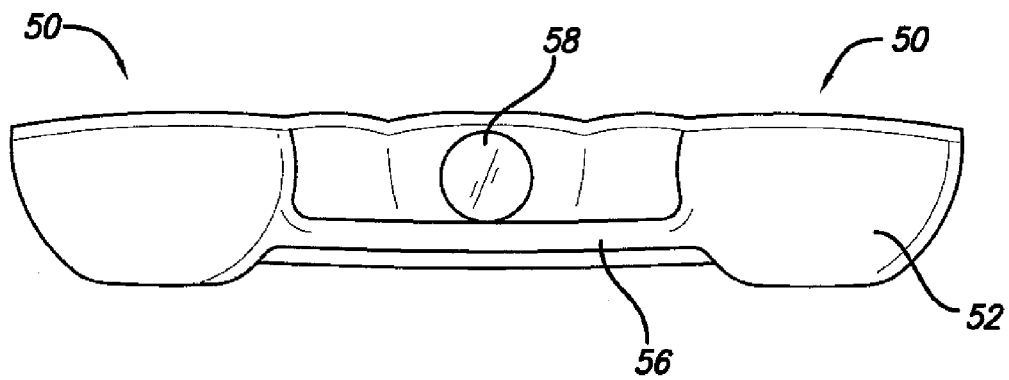
FIG. 7 is a rear elevation view of another embodiment of the invention.
Figure 8:
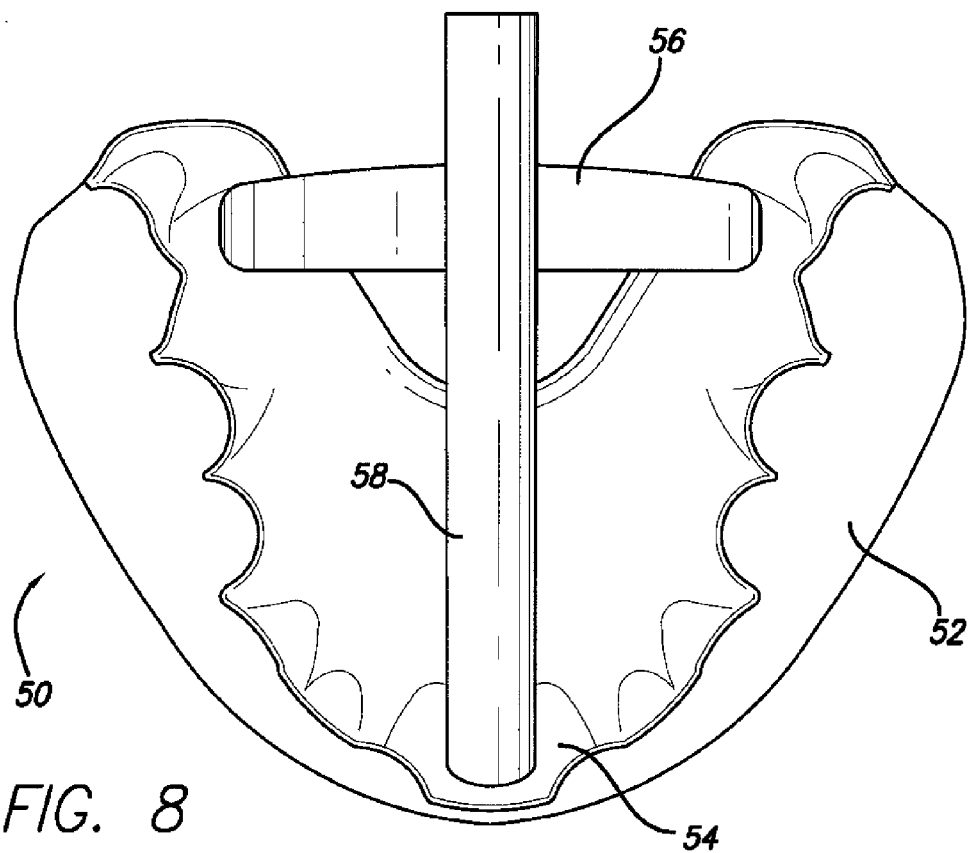
FIG. 8 is a bottom view of the embodiment of FIG. 7.

Referring now to FIGS. 7 and 8, there is shown another embodiment of an appliance 50 with a body 52 and an anterior strip or ramp 54. This appliance is adapted to fit over the upper teeth, similar to the first embodiment described above. Body 52 is made entirely of an acrylic plastic, commonly used for dental devices, and is custom fitted to fit over the upper posterior teeth in the same manner as an occlusal night guard, which uses an occlusal coverage. The occlusal coverage holds appliance 50 firmly onto the upper posterior teeth.

Transpalatal bar 56 inhibits the upward and backward movement of the tongue as described for the first embodiment.

Anterior tongue restrainer 58 extends from raised anterior strip 54 past transpalatal bar 56, to further inhibit and restrain the upward and backward movement of the tongue. Anterior tongue restrainer 56 in this embodiment is cylindrical and straight, and may be attached to the transpalatal bar by the use of acrylic. Anterior tongue restrainer 58 extends past transpalatal bar 56 to a length determined by the needs of the patient. However anterior tongue restrainer 58 does not touch the tongue in its normal state. It also does not touch the palate. It does help to inhibit and restrain the upward and backward movement of the tongue during sleep.

Figure 9:
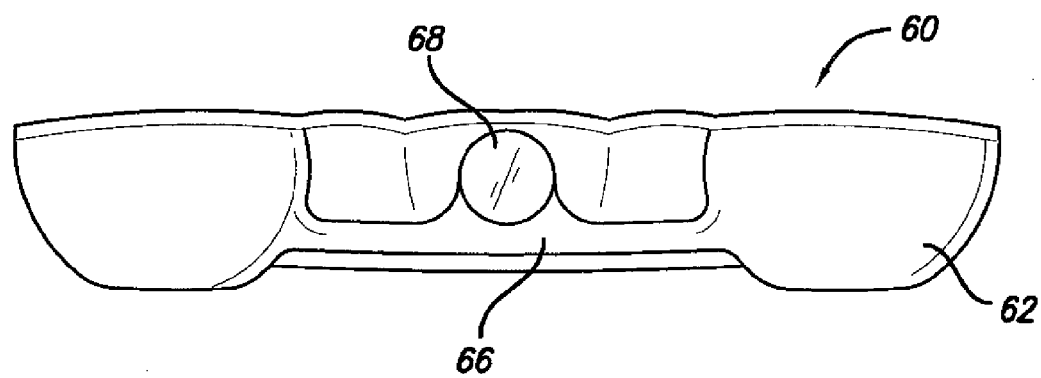
FIG. 9 is a rear elevation view of another embodiment of the invention; and, FIG. 10 is a bottom view of the embodiment of FIG. 9.
Figure 10:
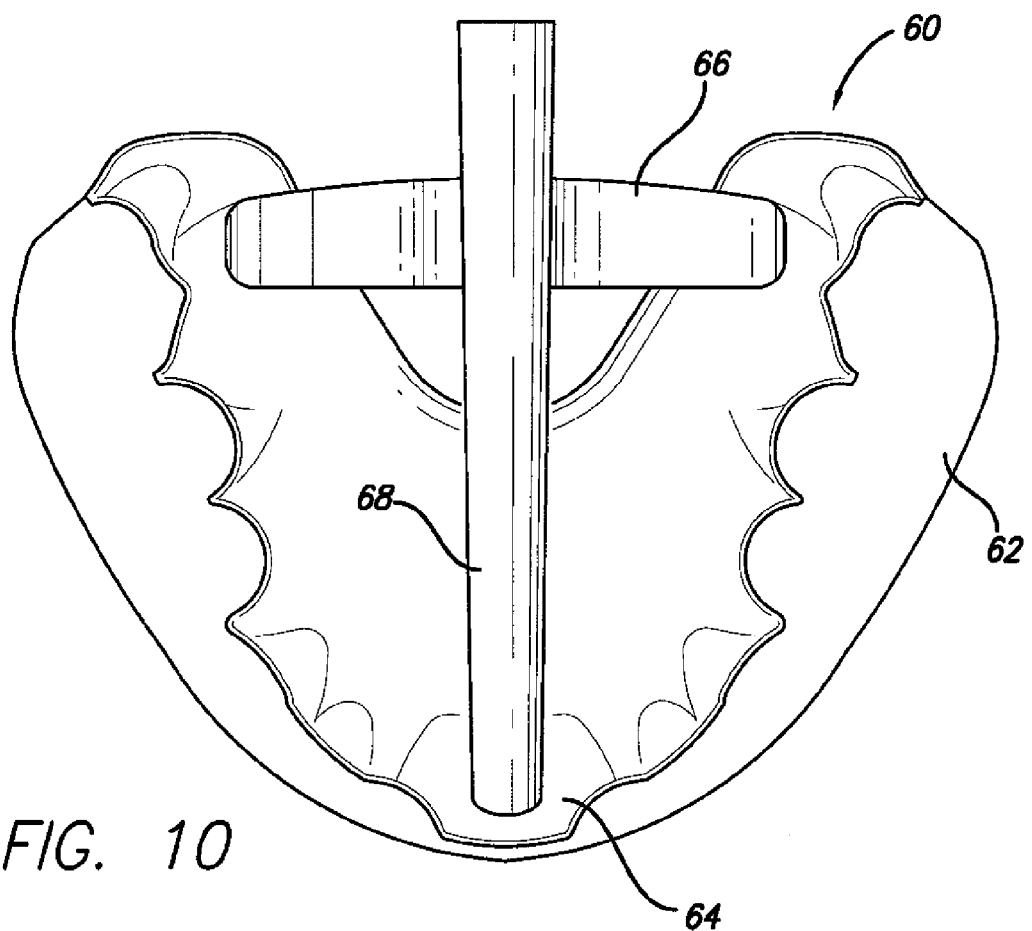

Referring now to FIGS. 9 and 10, there is shown another embodiment of an appliance 60 with a body 62 and an anterior strip or ramp 64. This appliance is adapted to fit over the upper teeth, similar to the first embodiment described above. Body 62 is made entirely of an acrylic plastic, commonly used for dental devices, and is custom fitted to fit over the upper posterior teeth in the same manner as an occlusal night guard, which uses an occlusal coverage. The occlusal coverage holds appliance 60 firmly onto the upper posterior teeth.

Transpalatal bar 66 inhibits the upward and backward movement of the tongue as described for the first embodiment.

In this embodiment, anterior tongue restrainer 68 and transpalatal bar 66 are manufactured as a single unit from an acrylic plastic. Anterior tongue restrainer 68 extends from raised anterior strip 64 past transpalatal bar 66, to further inhibit and restrain the upward and backward movement of the tongue. Anterior tongue restrainer 56 in this embodiment is cylindrical and straight and also gradually expands to a larger diameter as it extends from the front of the appliance to the rear. This is helpful for some patients in reducing snoring and sleep apnea. Anterior tongue restrainer 68 extends past transpalatal bar 66 to a length determined by the needs of the patient. However anterior tongue restrainer 68 does not touch the tongue in its normal state. It also does not touch the palate. It does help to inhibit and restrain the upward and backward movement of the tongue during sleep.

On any of the above-described embodiments, if it is necessary to advance the mandible to increase the airway even more, acrylic is added to the most lingual portion of the anterior ramp, creating a projection wall that comes off of the anterior ramp at 90 degrees. The lower anterior teeth swing forward and bite forward of this lingual wall. This results in the mandible coming forward to obtain an increased opening.

With a device having posterior ramps, a baseplate is placed over the right and left posterior ramps, anywhere from the $2^{nd}$ molar to the $1^{st}$ bicuspid and locked in place with acrylic. In each instance the lower teeth are advanced forward up to 2 mm past the upper teeth.

All of the devices described herein, which are totally or partially made of plastic, are preferably made of acrylic plastic or talon plastic.

The presence or absence of the posterior tongue restrainer or the posterior projections, as well as the particular type of appliance from the various embodiments shown, is chosen based upon what works best for the individual patient.

The transpalatal bar and the anterior tongue restrainers described in all the embodiments herein do not touch the tongue in its normal state and do not touch the palate, so that there is a gap between the transpalatal bar and the tongue and a gap between the transpalatal bar and the palate. There is also a gap between the anterior tongue restrainer and the tongue in its normal position and the anterior tongue restrainer and the palate. Even the posterior projections and posterior tongue restrainer, if present, do not touch the tongue in its normal position or the palate, so that there is a gap between. All of the elements shown are designed to inhibit and restrain the upward and backward movement of the tongue but be comfortable for the patient to wear.

Having thus described the invention, it is requested that the invention be described by the scope of the following claims.

I claim:

1. A dental oral appliance to open the airway for a sleeping individual who suffers with snoring or obstructive sleep apnea comprising, a body portion covering the upper or lower teeth, said body having an open palate, means to removably affix the appliance to the upper or lower teeth, means to prevent occlusion of the upper and lower teeth, a transpalatal bar that extends from the inside of the right molars to the inside of the left molars to inhibit the upward and backward movement of the tongue, and an anterior tongue restrainer attached at one end to the transpalatal bar and at the other end to a front of the body portion.

2. The dental oral appliance of claim 1 in which the transpalatal bar is curved upwards over the tongue.

3. The dental oral appliance of claim 1 in which the anterior tongue restrainer is curved downward.

4. The dental oral appliance of claim 1 in which the means to removably affix the appliance to the upper or lower teeth comprises an occlusal coverage.

5. The dental oral appliance of claim 1 in which the means to prevent occlusion of the upper and lower teeth comprises a raised incisor ramp that extends from two or more incisors toward the lingual.

6. The dental oral appliance of claim 1 in which the means to prevent occlusion of the upper and lower teeth comprises raised posterior ramps.

7. The dental oral appliance of claim 1 further comprising a posterior tongue restrainer attached to the transpalatal bar.

8. The dental oral appliance of claim 1 in which the appliance is made of acrylic plastic.

9. The dental oral appliance of claim 1 further comprising means to advance the mandible.

10. A dental oral appliance to open the airway for a sleeping individual who suffers with snoring or obstructive sleep apnea comprising, a body portion covering the upper or lower teeth, said body having an open palate, means to removably affix the appliance to the upper or lower teeth, means to prevent occlusion of the upper and lower teeth, a transpalatal bar that extends from the inside of the right molars to the inside of the left molars to inhibit the upward and backward movement of the tongue, and an anterior tongue restrainer attached at one end to the transpalatal bar and at the other end to a front of the body portion, further comprising a plurality of raised projections on the bottom of the transpalatal bar.

11. A dental oral appliance to open the airway for a sleeping individual who suffers with at least one of snoring and obstructive sleep apnea, comprising, a body, structure configured to removably affix the appliance to the upper teeth, structure configured to prevent occlusion of the upper and lower teeth, a transpalatal member configured to provide a gap between the transpalatal member and the palate, and a gap between the transpalatal member and the tongue, extending from the inside of one or more of the upper right molars to the inside of one or more of the upper left molars, to restrain the tongue from upward and backward movement and an anterior tongue restrainer attached at one end to the transpalatal member and at the other end to an anterior portion of the body, to further restrain the tongue from upward and backward movement, said anterior tongue restrainer configured to not touch the palate or the tongue in its normal position.

12. The dental oral appliance of claim 11 in which the structure to removably affix the appliance to the upper teeth comprises an occlusal coverage.

13. The dental oral appliance of claim 12 in which the anterior tongue restrainer has a gradually increasing diameter from the front to the rear.

14. The dental oral appliance of claim 11 in which the structure to prevent occlusion of the upper and lower teeth comprises a raised incisor ramp that extends from two or more incisors to the lingual.

15. The dental oral appliance of claim 11 in which the structure to prevent occlusion of the upper and lower teeth comprises raised posterior ramps.

16. The dental oral appliance of claim 11 in which the transpalatal member is curved upwards over the tongue.

17. The dental oral appliance of claim 11 in which the anterior tongue restrainer is curved downward.

18. The dental oral appliance of claim 11 further comprising a posterior tongue restrainer attached to the transpalatal member.

19. The dental oral appliance of claim 11 in which the entire appliance is made of an acrylic plastic.

20. The dental oral appliance of claim 11 further comprising structure to advance the mandible.

21. The dental oral appliance of claim 11 in which the anterior tongue restrainer is cylindrical in shape.

22. A dental oral appliance to open the airway for a sleeping individual who suffers with at least one of snoring and obstructive sleep apnea, comprising, a body, structure configured to removably affix the appliance to the upper teeth, structure configured to prevent occlusion of the upper and lower teeth, a transpalatal member configured to provide a gap between the transpalatal member and the palate, and a gap between the transpalatal member and the tongue, extending from the inside of one or more of the upper right molars to the inside of one or more of the upper left molars, to restrain the tongue from upward and backward movement and an anterior tongue restrainer attached at one end to the transpalatal bar and at the other end to the body, further comprising a plurality of raised projections on the bottom of the transpalatal bar.

23. A dental oral appliance to open the airway for a sleeping individual who suffers with at least one of snoring and obstructive sleep apnea, comprising, a body, structure configured to removably affix the appliance to the upper or lower teeth, a raised incisor ramp that extends from two or more incisors to the lingual to prevent occlusion of the upper and lower teeth, a transpalatal member configured to provide a gap between the transpalatal member and the palate, and a gap between the transpalatal member and the tongue, extending from the inside of one or more of the upper right molars to the inside of one or more of the upper left molars, to restrain the tongue from upward and backward movement and an anterior tongue restrainer extending from the transpalatal member to the raised incisor ramp to further restrain the tongue from upward and backward movement, said anterior tongue restrainer configured to not touch the palate or the tongue in its normal position.

24. The dental oral appliance of claim 23 in which the transpalatal member is curved upwards over the tongue.

25. The dental oral appliance of claim 23 in which the anterior tongue restrainer is curved downward.

26. The dental oral appliance of claim 23 further comprising a posterior tongue restrainer attached to the transpalatal member.

27. The dental oral appliance of claim 23 in which the entire appliance is made of an acrylic plastic.

28. The dental oral appliance of claim 23 further comprising structure to advance the mandible.

29. The dental oral appliance of claim 23 in which the anterior tongue restrainer is cylindrical in shape.

30. The dental oral appliance of claim 23 in which the anterior tongue restrainer has a gradually increasing diameter from the front to the rear.

* * * * *